United States Patent
Alsum et al.

(10) Patent No.: US 8,318,986 B2
(45) Date of Patent: Nov. 27, 2012

(54) METHODS FOR IMPROVING SYNGAS-TO-ALCOHOL CATALYST ACTIVITY AND SELECTIVITY

(75) Inventors: Patrick J. Alsum, Loveland, CO (US); Esther M. Wilcox, Longmont, CO (US); Jesse E. Hensley, Arvada, CO (US); Karl Kharas, Louisville, CO (US)

(73) Assignee: Albemarle Corporation, Baton Rouge, LA (US)

( * ) Notice: Subject to any disclaimer, the term of this patent is extended or adjusted under 35 U.S.C. 154(b) by 554 days.

(21) Appl. No.: 12/565,944

(22) Filed: Sep. 24, 2009

(65) Prior Publication Data

US 2010/0076228 A1  Mar. 25, 2010

Related U.S. Application Data

(60) Provisional application No. 61/100,024, filed on Sep. 25, 2008.

(51) Int. Cl.
*C07C 31/08* (2006.01)
*B01J 27/51* (2006.01)

(52) U.S. Cl. ......... 568/840; 502/216; 502/220; 502/222

(58) Field of Classification Search .................. 568/840; 502/216, 220, 222
See application file for complete search history.

(56) References Cited

U.S. PATENT DOCUMENTS

| | | | |
|---|---|---|---|
| 4,752,623 | A | 6/1988 | Stevens |
| 5,004,717 | A | 4/1991 | Lee et al. |
| 6,322,849 | B2 | 11/2001 | Joshi et al. |
| 6,812,179 | B2 | 11/2004 | Huang et al. |
| 2007/0010588 | A1 | 1/2007 | Pearson |

FOREIGN PATENT DOCUMENTS

WO  03002252  1/2003

OTHER PUBLICATIONS

S. Phillips et al., "Thermochemical Ethanol via Indirect Gasification and Mixed Alcohol Synthesis of Lignocellulosic Biomass", NREL Technical Report/TP-510-41168 (Apr. 2007).

*Primary Examiner* — Sikarl Witherspoon
(74) *Attorney, Agent, or Firm* — Jeremy J. Kliebert; Marcy M. Hoefling; James A. Jubinsky

(57) ABSTRACT

The invention herein provides methods of activating a catalyst composition. These methods include annealing a catalyst with an inert gas, under effective conditions, and then contacting the annealed catalyst with syngas to produce an activated catalyst. These steps can also be reversed. The activated catalysts can be employed to convert syngas into products, such as alcohols, with improved selectivities and yields.

39 Claims, 6 Drawing Sheets

METHODS FOR IMPROVING SYNGAS-TO-ALCOHOL CATALYST ACTIVITY AND SELECTIVITY

PRIORITY DATA

This patent application claims priority under 35 U.S.C. §120 from U.S. Provisional Patent Application No. 61/100,024 for "METHODS FOR IMPROVING SYNGAS-TO-ALCOHOL CATALYST ACTIVITY AND SELECTIVITY," filed Sep. 25, 2008, the disclosure of which is hereby incorporated by reference herein for all purposes.

FIELD OF THE INVENTION

The present invention generally relates to the field of catalysts and methods for producing alcohols from synthesis gas.

BACKGROUND OF THE INVENTION

In materials science, it is known that heat treatments can be used to alter the physical and/or chemical properties of a material. Heat-treatment techniques generally include annealing, case hardening, precipitation strengthening, tempering, and quenching. Annealing causes changes in material properties by heating and maintaining a suitable temperature Annealing can occur by the diffusion of atoms within a solid material Annealing can be used to induce ductility, relieve internal stresses, refine structure, and improve cold working properties.

It is recognized in some materials-science arts that annealing can be performed with inert gases. For example, U.S. Pat. No. 6,322,849, to Joshi et al., describes an inert-gas anneal to restore desired electronic and ferroelectric properties of a ferroelectric element. The inert-gas anneal is preferably performed after hydrogen-plasma processes, forming-gas anneal steps, and other high-energy steps of integrated circuit formation.

Synthesis gas (hereinafter referred to as syngas) is a mixture of hydrogen ($H_2$) and carbon monoxide (CO). Syngas can be produced, in principle, from virtually any material containing carbon. Carbonaceous materials commonly include fossil resources such as natural gas, petroleum, coal, and lignite; and renewable resources such as lignocellulosic biomass and various carbon-rich waste materials. It is preferable to utilize a renewable resource to produce syngas because of the rising economic, environmental, and social costs associated with fossil resources.

There exist a variety of conversion technologies to turn these feedstocks into syngas. Conversion approaches can utilize a combination of one or more steps comprising gasification, pyrolysis, steam reforming, and/or partial oxidation of a carbon-containing feedstock.

Syngas is a platform intermediate in the chemical and biorefining industries and has a vast number of uses. Syngas can be directly combusted to produce heat and power. Syngas can also be converted into alkanes, olefins, oxygenates, and alcohols such as methanol, ethanol, and higher alcohols. These chemicals can be blended into, or used directly as, diesel fuel, gasoline, and other liquid fuels.

Since the 1920s it has been known that mixtures of methanol, ethanol, and other linear alcohols can be obtained by reacting syngas over certain catalysts (Fischer and Tropsch, *Brennst.-Chem.* 7:97, 1926). Later, Dow Chemical and Union Carbide jointly developed a sulfided mixed-alcohol catalyst based on $MoS_2$ (Phillips et al., National Renewable Energy Laboratory TP-510-41168, April 2007). U.S. Pat. No. 4,752,623 (Stevens and Conway), originally assigned to Dow Chemical, discloses a cobalt-molybdenum-sulfide catalyst for producing mixed alcohols from syngas. However, known catalysts used for the conversion of syngas to alcohols can have limited yields and selectivities to particular alcohols (such as ethanol).

What are therefore needed are methods to increase yields and selectivities to particular alcohols, especially $C_1$-$C_4$ alcohols. It would be particularly beneficial for such methods to be capable of treating catalyst compositions in a practical manner, such as inside a reactor.

SUMMARY OF THE INVENTION

The present invention addresses the need in the art by providing a catalyst treatment method comprising inert-gas annealing.

In one variation, the invention provides a method of activating a catalyst, the method comprising:

(a) annealing the catalyst with a first gas phase comprising an inert gas, under effective conditions including a first temperature and a first pressure, thereby producing an annealed catalyst; and (b) contacting the annealed catalyst with a second gas phase comprising syngas, under conditions comprising a second temperature and a second pressure, thereby producing an activated catalyst.

The inert gas can be selected from the group consisting of $N_2$, He, Ne, Ar, Kr, Xe, Rn, and combinations thereof. A preferred inert gas is He. In some embodiments, the annealing step comprises contacting the catalyst with not only an inert gas but also $H_2$, CO, or a mixture of $H_2$ and CO. The second gas phase comprising syngas can also include methane, carbon dioxide, and other gases.

In some embodiments, the first temperature is less than about 450° C., such as about 280-350° C. The first pressure can be less than about 200 atm, such as about 80-120 atm. The time for step (a) can be at least five hours, or some other effective time.

In some embodiments, the second temperature is selected from about 150-350° C., such as about 250-325° C. The second pressure can be selected from about 30-200 atm, such as about 80-120 atm.

In some embodiments, the first temperature and the second temperature are about the same. Also, the first pressure and the second pressure can be about the same. Certain embodiments employ a plurality of increasing temperatures between the first and second temperatures, and further a plurality of increasing pressures between the first and second pressures. Steps (a) and (b) can be conducted in the same vessel.

Some variations further employ step (c), converting syngas to at least one $C_1$-$C_4$ alcohol over the activated catalyst. Such a catalyst can comprise cobalt, molybdenum, sulfur, and potassium, for example. Steps (a), (b), and (c) can all be conducted in the same vessel.

The converting in step (c) can be conducted at a temperature that is about the same as the first temperature, and can further be conducted at a pressure that is about the same as the first pressure. Or, the converting step can operate with a temperature and pressure that are the same as those in step (b).

In some embodiments, at least one $C_1$-$C_4$ alcohol includes ethanol. According to the invention set forth herein, the selectivity and/or yield of ethanol produced by the activated catalyst can be higher than the selectivity and/or yield of ethanol that would have been produced in the absence of step (a). The selectivity of $CO_2$ produced by the activated catalyst can be lower than the selectivity of $CO_2$ that would have been produced in the absence of step (a).

The order of steps can vary. Specifically, in another variation, this invention provides a method of activating a catalyst, the method comprising:

(a) contacting the catalyst with a first gas phase comprising syngas, under conditions comprising a first temperature and a first pressure, thereby producing a pre-activated catalyst; and (b) annealing the pre-activated catalyst with a second gas phase consisting essentially of an inert gas, under effective conditions comprising a second temperature and a second pressure, thereby producing an activated catalyst.

In a certain embodiment, the present disclosure describes a method of activating a Co/Mo/S/K catalyst, the method comprising:

(a) annealing the catalyst with helium at a temperature of about 310° C. and a pressure of about 1270 psi, thereby producing an annealed catalyst; and (b) contacting the annealed catalyst with syngas at a temperature of about 280° C. and a pressure of about 1270 psi, thereby producing an activated Co/Mo/S/K catalyst.

Another aspect of this invention relates to catalyst compositions produced according to the methods herein. Certain embodiments relate to new compositions such as activated catalysts produced according to any of the methods described herein.

Yet another aspect of the present invention provides a method of producing an annealed catalyst intermediate, the method comprising:

(a) providing an effective starting catalyst composition; and (b) annealing the starting catalyst composition with a first gas phase comprising an inert gas, under effective conditions, thereby producing an annealed catalyst intermediate.

The inert gas can be selected from the group consisting of $N_2$, He, Ne, Ar, Kr, Xe, Rn, and combinations thereof. The annealing step can include contacting the catalyst with $H_2$, CO, or a mixture of $H_2$ and CO. The annealing step can also include contacting the catalyst with other gases, such as (but not limited to) $CO_2$ and $CH_4$.

Effective conditions include a temperature of less than about 450° C., such as about 280-350° C. Effective conditions include a pressure of less than about 200 atm, such as about 80-120 atm. Step (b) (annealing) can be conducted for any effective amount of time, such as five hours or more.

The annealed catalyst intermediate comprises cobalt, molybdenum, sulfur, and potassium, in some embodiments.

Some methods further include using the annealed catalyst intermediate. One use is to generate an activated (or otherwise suitable) catalyst from the annealed catalyst intermediate to convert syngas to at least one $C_1$-$C_4$ alcohol, such as ethanol. The selectivity and/or yield of ethanol can be higher than the selectivity and/or yield of ethanol that would have been produced in the absence of annealing.

DETAILED DESCRIPTION OF EMBODIMENTS OF THE INVENTION

Figure 1:
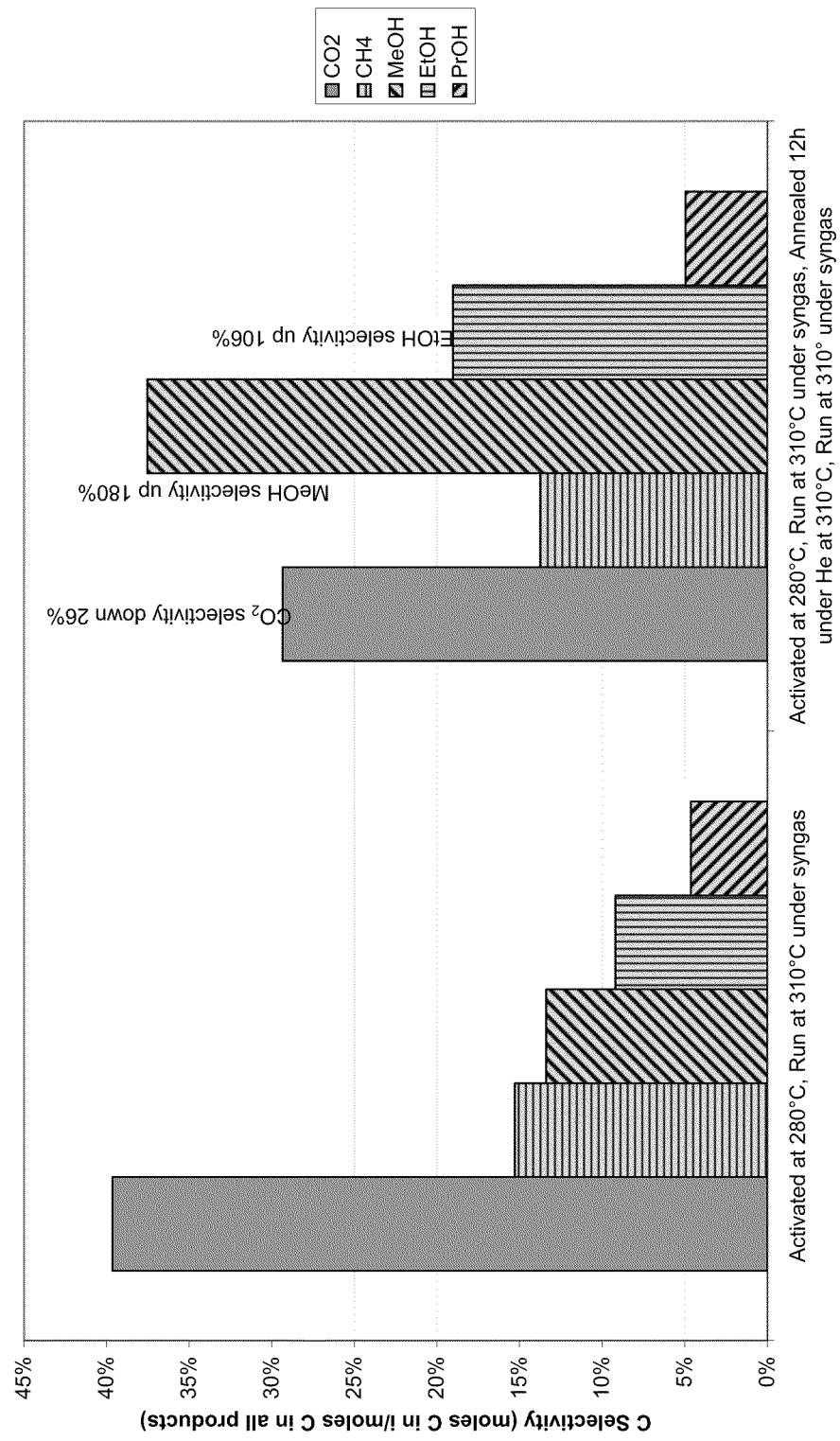
FIG. 1 shows experimental data depicting carbon selectivities before and after treatment with He, post-activation, in some embodiments.

This description will enable one skilled in the art to make and use the invention, and it describes several embodiments, adaptations, variations, alternatives, and uses of the invention, including what is presently believed to be the best mode of carrying out the invention.

As used in this specification and the appended claims, the singular forms "a," "an," and "the" include plural referents unless the context clearly indicates otherwise. Unless defined otherwise, all technical and scientific terms used herein have the same meaning as is commonly understood by one of ordinary skill in the art to which this invention belongs.

Unless otherwise indicated, all numbers expressing reaction conditions, stoichiometries, concentrations of components, and so forth used in the specification and claims are to be understood as being modified in all instances by the term "about." Accordingly, unless indicated to the contrary, the numerical parameters set forth in the following specification and attached claims are approximations that may vary depending at least upon the specific analytical technique. Any numerical value inherently contains certain errors necessarily resulting from the standard deviation found in their respective testing measurements.

As used herein, "$C_1$-$C_4$ alcohols" means one or more alcohols selected from methanol, ethanol, propanol, and butanol, including all known isomers of such compounds.

The present invention will now be described by reference to the following detailed description and accompanying drawings which characterize and illustrate some preferred embodiments for producing ethanol. This description by no means limits the scope and spirit of the present invention. For example, preferred embodiments relate to Co/Mo/S catalyst compositions, but the invention is by no means so limited.

The present invention is premised, at least in part, on the surprising realization that heated inert gases can be used to effectively anneal catalyst compositions. Without being limited to any particular mechanism or theory, it is presently believed that inert gases can, during such annealing, modify the molecular migration of atoms on the catalyst surface, or open additional or certain active catalyst sites.

Annealing can be a beneficial part of an overall catalyst activation (or re-activation) method. Annealing can lead to higher catalyst activity, better product selectivities, or both of these enhancements. It should be noted that an annealed catalyst (without further activation) may have some of the desired activity, for e.g. syngas to alcohols. An annealed catalyst can be subjected to further activation steps, or it can be contacted directly with a process stream and allowed to activate (or re-activate) over some period of time within the reactor.

In some variations, the present invention provides methods for activating base-promoted Co/Mo/S catalysts for production of $C_1$-$C_4$ alcohols from syngas. These methods comprise annealing with one or more inert gases. An "inert gas" used in preferred methods should be substantially inert, but there can of course be trace contaminants present. Additionally, reactive gases (such as CO or $H_2$) can be present in conjunction with inert gases. For example, some embodiments employ mixtures of syngas and inert gas during the annealing step.

In some embodiments, an inert gas can be selected from the group consisting of He, Ne, Ar, Kr, Xe, Rn, or mixtures of any of these. Helium is preferred, in some embodiments. It is not preferred, but technically possible, to use Rn because of its radioactivity. In some embodiments, $N_2$ can be employed as the inert gas or as part of a mixture of inert gases.

In preferred embodiments, annealing is one step in a method of activating a catalyst. In these preferred embodiments, a catalyst is activated according to the following steps. First, a starting catalyst composition is annealed with a first gas phase comprising an inert gas, under effective conditions, thereby producing an annealed catalyst.

Effective conditions for annealing can include temperatures up to about 450° C., such as about 280-350° C. The present invention is not limited to any particular range of annealing temperatures. It will be appreciated by a skilled artisan that lower temperatures can be employed but will generally necessitate longer annealing times, because annealing is generally favored at higher temperatures. Practical materials considerations and process economics will tend to disfavor excessive temperatures, such as above about 450° C.

Effective pressures for annealing include pressures up to about 200 atm or more. In some embodiments, annealing pressures are selected from about 80-120 atm. In other embodiments, annealing pressures are less than 80 atm, such as about 20-50 atm, e.g. about 30 atm. Again, practical considerations can dictate preferred pressures. While higher pressures mean higher partial pressures (concentrations) of the inert gases present, and therefore potentially higher rates of annealing reactions (assuming positive-order kinetics), there is also a decrease in gas diffusivity with pressure. At least part of the annealing process may involve diffusion of inert gases into—or evolved gases out of—catalyst pores. Excessive pressures can limit these mass-transfer rates.

A second step of activating the catalyst is to contact the annealed catalyst with a second gas phase comprising syngas, under conditions comprising a second temperature and a second pressure, thereby producing an activated catalyst for the conversion of syngas to alcohols (or other desired chemistry). An "activated catalyst" can be a catalyst that is activated for the first time, or a catalyst that is re-activated following at least some deactivation.

In this second step, the temperature and pressure can be about the same as the annealing temperature and pressure, but that is by no means necessary. The second temperature can be selected from about 150-350° C., such as about 250-325° C. The second pressure can be selected from about 30-200 atm, such as about 80-120 atm.

In one embodiment, a plurality of increasing temperatures can be employed between the first and second temperatures, and further comprising a plurality of increasing pressures between the first and second pressures. Without being limited to a particular theory, this ramping of conditions from annealing to final catalyst activation can allow for various chemical and physical mechanisms to dominate (or be suppressed) at different temperatures and pressures. In a similar manner, other temperature and pressure programs can be utilized, as will be appreciated.

The amount of time that is preferred for the annealing step is not regarded as critical to the invention. The times will generally be a function of temperature, pressure, starting compositions, and desired activity, as will be recognized by a person of ordinary skill in the art. In various embodiments, annealing times can be less than 1 hour, between about 1-10 hours, or between about 10-50 hours. In certain embodiments, annealing times are at least 5 hours.

Similarly, the amount of time that is preferred for the overall catalyst activation method is not regarded as critical to the invention. In various embodiments, overall catalyst-activation times can be less than 1 hour, between about 1-10 hours, or between about 10-50 hours. The majority of the overall activation time can be for either the first (annealing) step or for the second step of contacting the annealed catalyst with syngas. As further described herein, these steps can be reversed.

Some embodiments of the present invention provide for convenient in situ annealing of a catalyst composition contained in a reactor. Through appropriate valving schemes, a starting catalyst composition can be activated, including annealing, as it rests within a reactor vessel. In general, a common reactor can be used for both the annealing step and the syngas-contacting step (if conducted).

Another aspect of the invention provides for use of activated catalyst materials produced by the present methods, in a reactor for synthesis of alcohols, such as ethanol. When alcohols are desired, suitable catalysts may include, but are not limited to, those disclosed in co-pending and commonly assigned U.S. patent application Ser. No. 12/166,167. Preferred catalysts increase the rate of formation, selectivity, and/or yield of alcohols. Preferred catalysts also minimize the formation of $CO_2$ and $CH_4$ under reaction conditions that produce alcohols from syngas.

Other suitable catalysts to be activated by the present methods may include alkali/ZnO/$Cr_2O_3$, Cu/ZnO, Cu/ZnO/$Al_2O_3$, CuO/CoO, CuO/CoO/$Al_2O_3$, Co/S, Mo/S, Co/Mo/S, Ni/S, Ni/Mo/S, Ni/Co/Mo/S, Rh/Ti/$SiO_2$, Rh/Mn/$SiO_2$, Rh/Ti/Fe/Ir/SiO2, Rh/Mn/MCM-41, Cu, Zn, Rh, Ti, Fe, Ir, and mixtures thereof. The addition of basic promoters (e.g., K, Li, Na, Rb, Cs, and Fr) increases the activity and selectivity of some of these catalysts for ethanol or other $C_{2+}$ alcohols. Basic promoters include alkaline-earth and rare-earth metals. Non-metallic bases can also serve as effective promoters, in some embodiments.

The reactor is any apparatus capable of being effective for producing at least one $C_1$-$C_4$ alcohol from the syngas stream fed. The reactor can be a single vessel or a plurality of vessels. The reactor contains at least one catalyst composition that tends to catalyze the conversion of syngas into alcohols. The "reactor" can actually be a series or network of several reactors in various arrangements. For example, in some variations, the reactor comprises a large number of tubes filled with one or more catalysts as provided herein.

The same reactor that is used for the annealing step, the syngas-contacting step, or both of these can be employed for converting syngas to alcohols using the activated catalyst.

The reactor for converting syngas into alcohols can be engineered and operated in a wide variety of ways. Operation that is substantially continuous and at steady state is preferable, but is not necessary to carry out the invention. The flow pattern can be substantially plug flow, substantially well-mixed, or a flow pattern between these extremes. The flow direction can be vertical-upflow, vertical-downflow, or horizontal. A vertical configuration can be preferable.

In some embodiments, fresh syngas is produced according to methods described in Klepper et al., "Methods and apparatus for producing syngas," U.S. patent application Ser. No. 12/166,167 (filed Jul. 1, 2008), the assignee of which is the same as the assignee of the present application. U.S. patent application Ser. No. 12/166,167 is hereby incorporated by reference herein in its entirety.

In some embodiments, conditions effective for producing alcohols from syngas include reactor temperatures from about 200-400° C., preferably about 250-350° C. Depending on the catalyst chosen, changes to reactor temperature can change conversions, selectivities, and catalyst stability. As is recognized in the art, increasing temperatures can sometimes be used to compensate for reduced catalyst activity over long operating times.

Preferably, the syngas entering the reactor is compressed. Generally, catalyst productivity increases with increasing partial pressures of reactants. High reactor-inlet pressures realized by the presence of large quantities of unreactive gases are less preferable compared to higher partial pressures of the rate-limiting reactant(s). Conditions effective for producing alcohols from syngas include hydrogen and carbon monoxide partial pressures each about 10-200 atm or higher, preferably each about 25-100 atm. In some embodiments wherein $H_2$ is the rate-limiting reactant, it is beneficial to employ a higher partial pressure of $H_2$ than that of CO.

The input partial pressures define the feed hydrogen—carbon monoxide molar ratio ($H_2$/CO). While reaction rates are a function of species partial pressures, it can be a matter of convenience to specify $H_2$/CO for reasons of control and optimization within a certain process region. In some embodiments, conditions effective for producing alcohols from syngas include $H_2$/CO from about 0.2-4.0, preferably about 0.5-2.0, and more preferably about 0.5-1.5. These ratios are indicative of certain embodiments and are by no means limiting. It is possible to operate at feed $H_2$/CO ratios less than 0.2 as well as greater than 4, including 5, 10, or even higher.

In various embodiments, the feed to the reactor can include not only syngas but also one or more gases such as carbon dioxide, methane, ethane, ethylene, propane, propylene, methanol, ethanol, propanol, and higher hydrocarbons.

In some embodiments, conditions effective for producing alcohols from syngas include average reactor residence times from about 0.1-10 seconds, preferably about 0.5-2 seconds. "Average reactor residence time" is the mean of the residence-time distribution of the reactor contents under actual operating conditions. Catalyst contact times can also be calculated by a skilled artisan and these times will typically also be in the range of 0.1-10 seconds, although it will be appreciated that it is certainly possible to operate at shorter or longer times.

The catalyst phase can be a packed bed or a fluidized bed. The catalyst particles can be sized and configured such that the chemistry is, in some embodiments, mass-transfer-limited or kinetically limited. The catalyst can take the form of a powder, pellets, granules, beads, extrudates, and so on. When a catalyst support is optionally employed, the support may assume any physical form such as pellets, spheres, monolithic channels, etc. The supports may be coprecipitated with active metal species; or the support may be treated with the catalytic metal species and then used as is or formed into the aforementioned shapes; or the support may be formed into the aforementioned shapes and then treated with the catalytic species.

In general, the specific selection of catalyst configuration (geometry), temperature, partial pressures of both reactants and unreactive species, and residence time (or feed rate) will be selected to provide, or will be subject to constraints relating to, an economically optimized process. The plurality of reactor variables and other system parameters can be optimized, in whole or in part, by a variety of means.

Certain embodiments and aspects of the present invention will now be further described by way of the following examples.

EXAMPLE 1

A catalyst is prepared wherein the catalyst composition comprises Co and Mo, combined with atomic ratio of Co to Mo of about 0.5. The catalyst composition also comprises sulfur, in an atomic ratio of S to (Co+Mo) of about 2. Potassium is introduced as $K_2CO_3$ so that the atomic ratio of K to (Co+Mo) is about 0.4. Thus 10 g of catalyst powder having a formula $Co_1Mo_2S_6$ is promoted by the addition of 1.9 g of $K_2CO_3$ (anhydrous). This catalyst composition is subjected to various methods of the invention as described in these examples.

EXAMPLE 2

Figure 2:
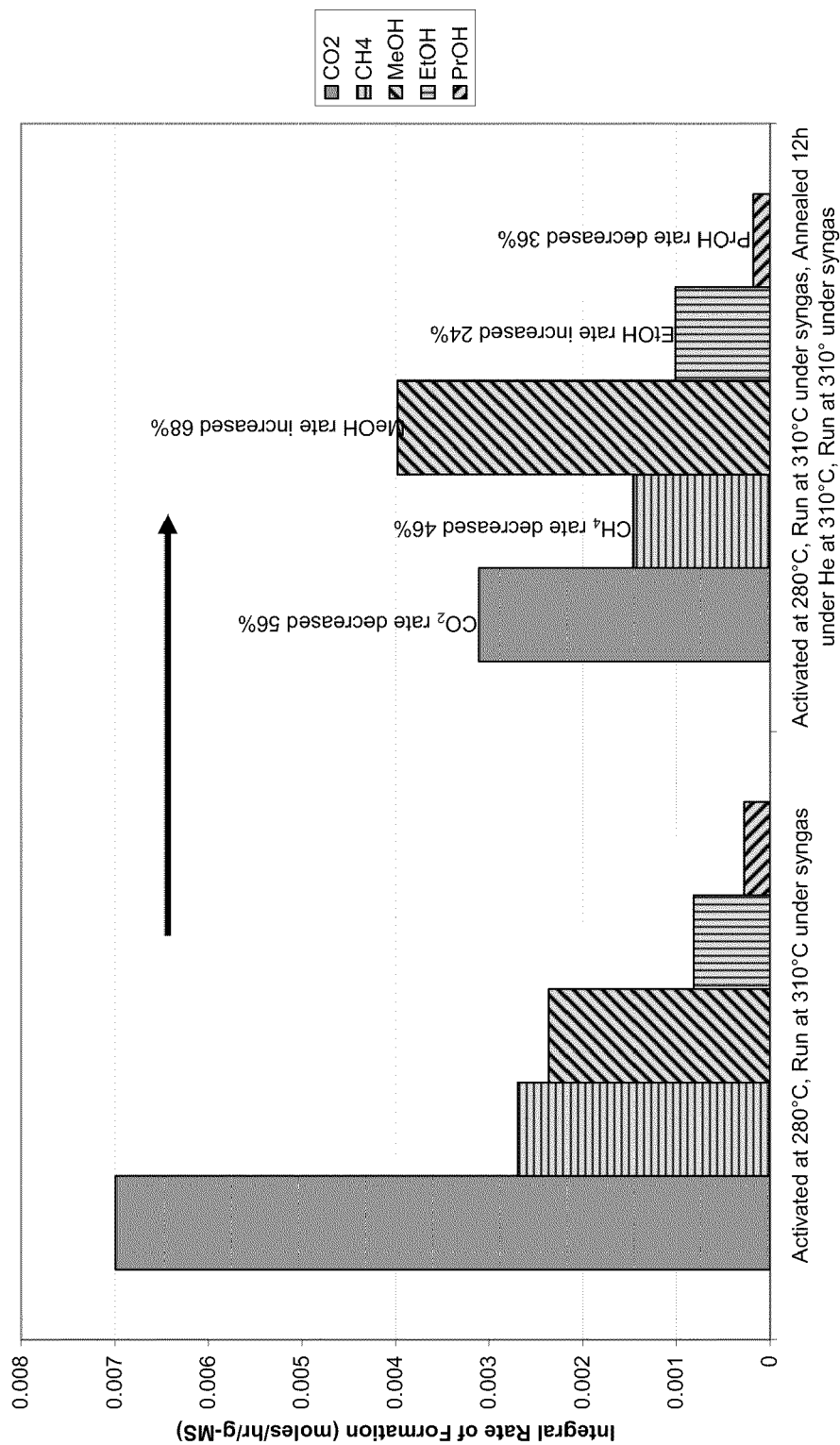
FIG. 2 shows experimental data depicting formation rates before and after treatment with He, post-activation, in some embodiments.

The effect of treating the catalyst from Example 1 with He (helium) at 310° C. and 1270 psi (86.4 atm) is shown in FIGS. 1 and 2. The figure shows data collected from the same catalyst, run in the same reactor, with the same feed gas composition, temperature, space velocity, and pressure, and with less than a single day period between measurements (Run 0053). The reactor is not unloaded between measurements. The data differ in that the catalyst is held under He at 310° C. and 1270 psi for 12 hours between repeat measurements. The change in catalyst activity is significant: a 26% reduction in $CO_2$ selectivity and a 180% and 106% increase in selectivity for methanol and ethanol, respectively. The rates of formation for methanol and ethanol increase by 68% and 24%, respectively.

EXAMPLE 3

Figure 3:
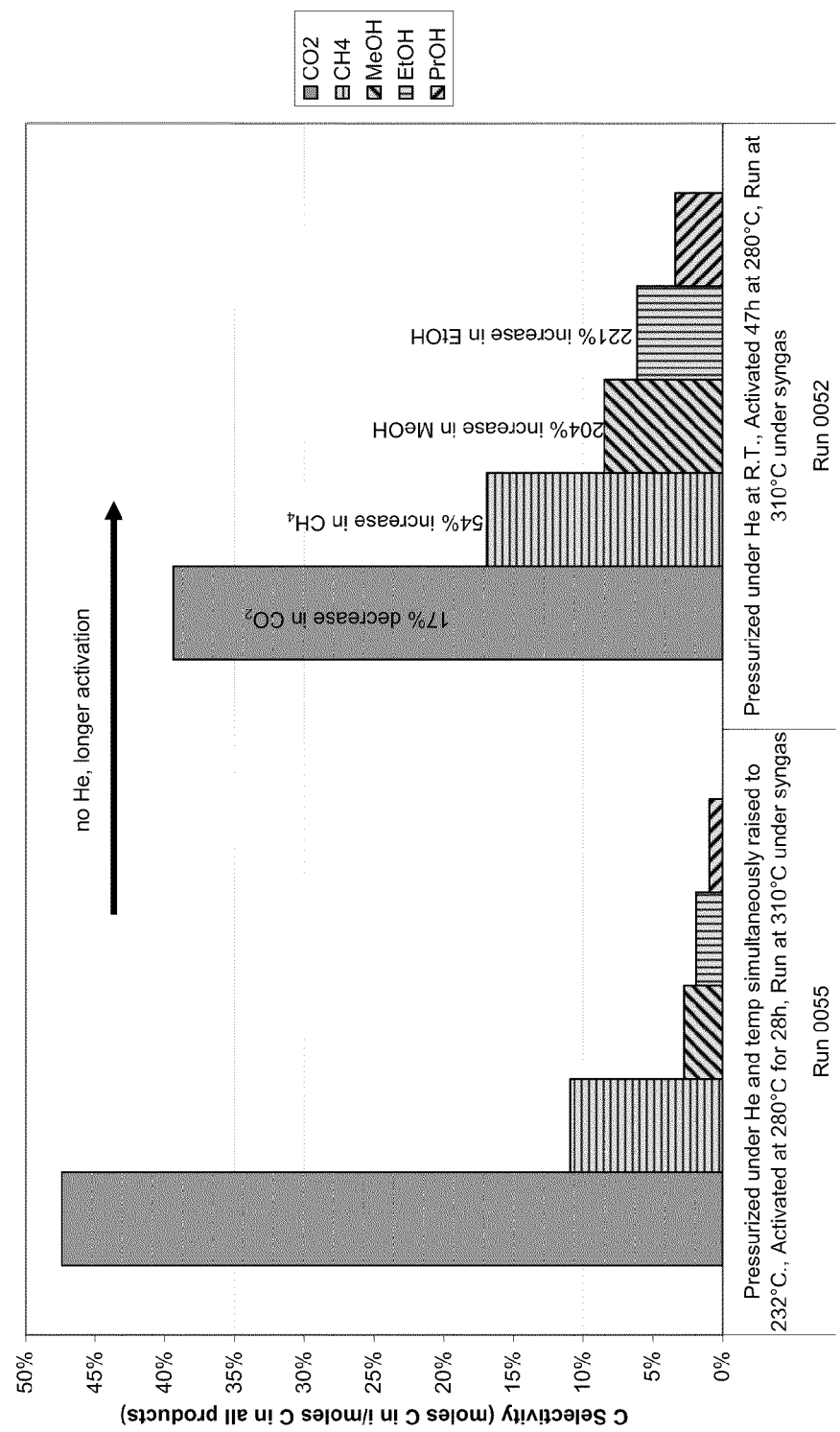
FIG. 3 shows experimental data depicting carbon selectivities at 310° C. with different activation times, in some embodiments.
Figure 4:
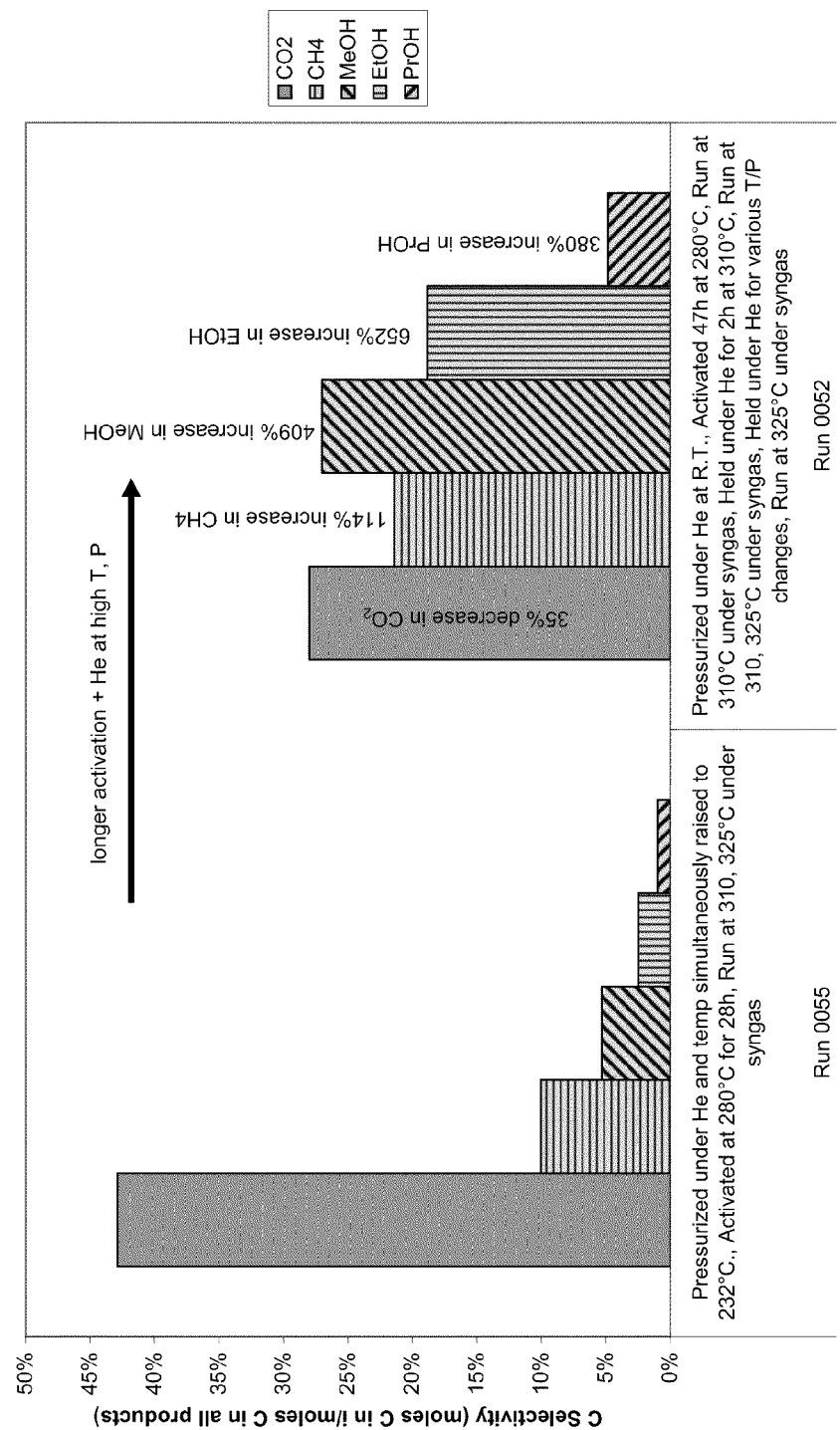
FIG. 4 shows experimental data depicting carbon selectivities at 325° C. with and without additional He treatment, in some embodiments.

FIGS. 3 and 4 show a further comparison of the effects of He treatment on a catalyst prepared according to Example 1. In the figures, data is shown for two aliquots of the same catalyst, run at different times, at the same conditions. In these figures, two phenomena can be addressed. First, one catalyst is activated for 28 h (Run 0055) while the second is activated for 47 h (Run 0052) under synthesis gas. Second, in Run 0052, the catalyst is run at 310° C.; then treated in He for various periods at various temperatures and pressures; then run at 325° C. Both treatment procedures appear to have an effect on catalyst performance.

FIG. 3 suggests that longer activation periods improve the selectivity of the catalyst—away from $CO_2$ and toward alcohols. FIG. 4 suggests that the brief He treatments experienced by the catalyst in Run 0052 improve the selectivity of the catalyst further. The rates of formation and yields of alcohols (not shown) improve in an analogous fashion. It should be observed that the increase in selectivity, presumably caused by a longer activation period, is enhanced even further after He treatment.

EXAMPLE 4

Figure 5:
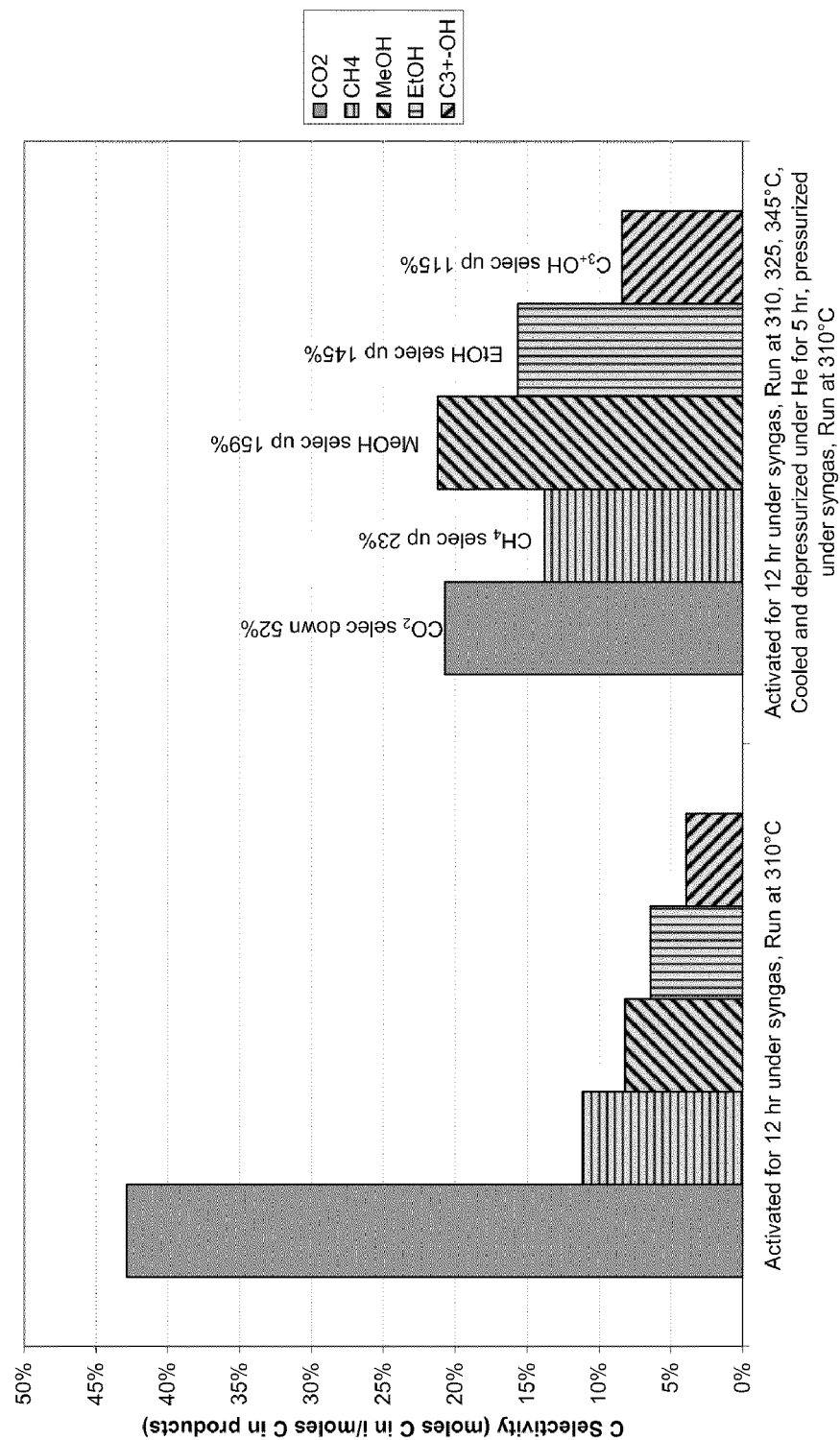
FIG. 5 shows experimental data depicting carbon selectivity after activation and before/after a brief period in He, in some embodiments.
Figure 6:
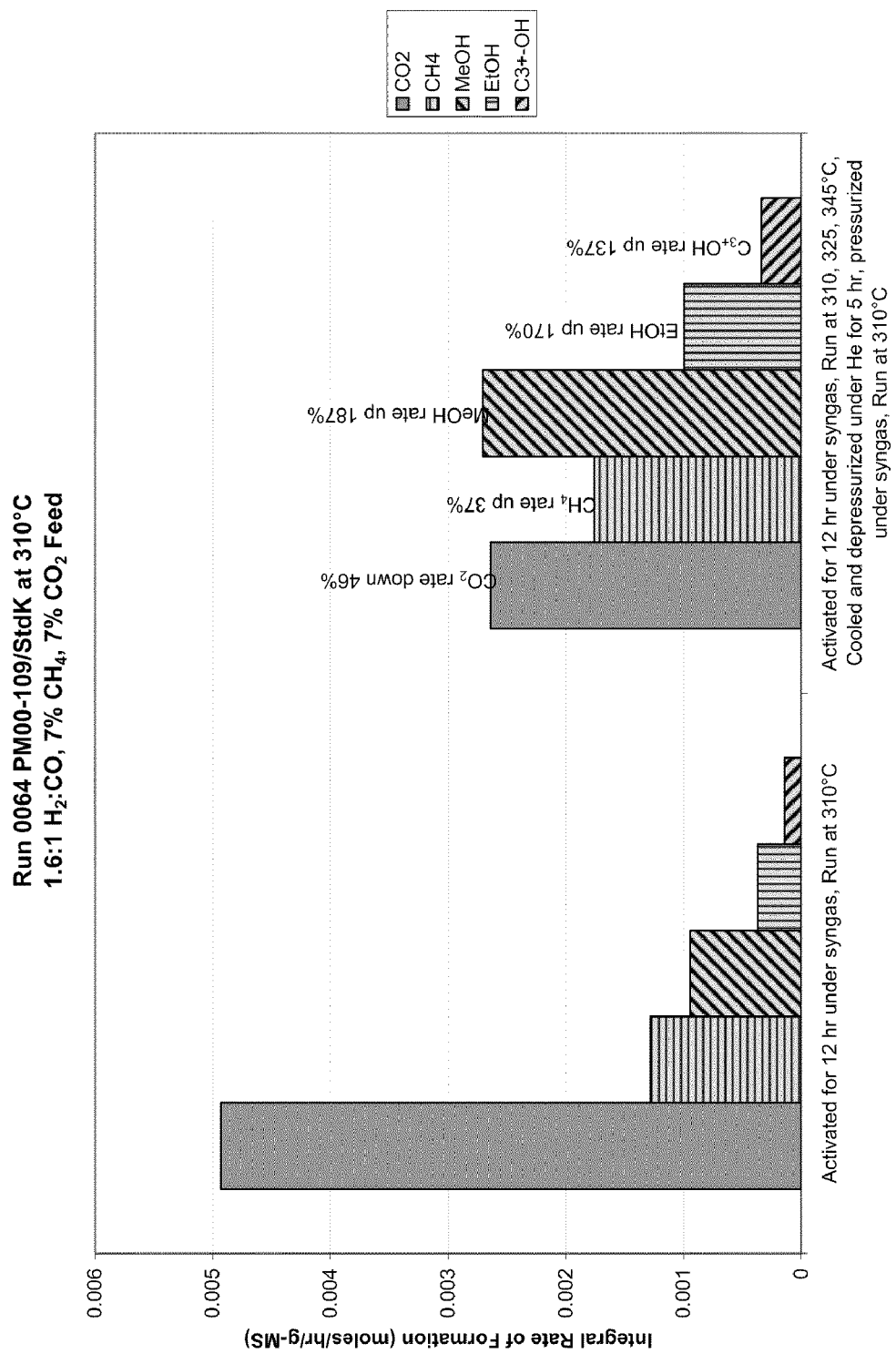
FIG. 6 shows experimental data depicting rates of formation after activation and before/after a brief period in He, in some embodiments.

FIGS. 5 and 6 depict improvements arising from a certain variation of the invention, which employs a catalyst prepared according to Example 1. The data (Run 0064) shown in FIGS. 5 and 6 suggest that treatments in He, conducted after a first step of catalyst activation, can improve catalyst activity. In FIGS. 5 and 6, reaction data is compared for runs at 310° C. before activation and after activation, runs at 310° C., 325° C., and 345° C., and 5 hours under He at steadily decreasing temperature and pressure.

It is evident that the catalyst selectivity shifts away from $CO_2$ and toward alcohols. The yield of alcohols, including ethanol, increases in kind In this detailed description, reference has been made to multiple embodiments of the invention and non-limiting examples relating to how the invention can be understood and practiced. Other embodiments that do not provide all of the features and advantages set forth herein may be utilized, without departing from the spirit and scope of the present invention. This invention incorporates routine experimentation and optimization of the methods and systems described herein. Such modifications and variations are considered to be within the scope of the invention defined by the claims.

All publications, patents, and patent applications cited in this specification are herein incorporated by reference in their entirety as if each publication, patent, or patent application were specifically and individually put forth herein.

Where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially.

Therefore, to the extent there are variations of the invention, which are within the spirit of the disclosure or equivalent to the inventions found in the appended claims, it is the intent that this patent will cover those variations as well. The present invention shall only be limited by what is claimed.

What is claimed is:

1. A method of activating a catalyst, said method comprising:
   (a) annealing said catalyst with a first gas phase comprising an inert gas, under effective conditions including a first temperature of less than about 450° C. and a first pressure of less than about 200 atm, thereby producing an annealed catalyst; and
   (b) contacting said annealed catalyst with a second gas phase comprising syngas, under conditions comprising a second temperature of from about 150° C. to about 350° C. and a second pressure of from about 30 atm to about 200 atm, thereby producing an activated catalyst.

2. The method of claim 1, wherein said inert gas is selected from the group consisting of $N_2$, He, Ne, Ar, Kr, Xe, Rn, and combinations thereof.

3. The method of claim 2, wherein said inert gas is He.

4. The method of claim 1, wherein said annealing step comprises contacting said catalyst with $H_2$, CO, or a mixture of $H_2$ and CO.

5. The method of claim 1, wherein said second gas phase further comprises methane and/or carbon dioxide.

6. The method of claim 1, wherein said first temperature is selected from about 280° C. to about 350° C.

7. The method of claim 1, wherein said first pressure is selected from about 80 atm to about 120 atm.

8. The method of claim 1, wherein said activated catalyst comprises cobalt, molybdenum, sulfur, and potassium.

9. The method of claim 1, wherein said second temperature is selected from about 250° C. to about 325° C.

10. The method of claim 1, wherein said second pressure is selected from about 80 atm to about 120 atm.

11. The method of claim 1, wherein step (a) is conducted for at least five hours.

12. The method of claim 1, further comprising (c) converting syngas to at least one $C_1$-$C_4$ alcohol over said activated catalyst.

13. The method of claim 1, wherein steps (a) and (b) are conducted in the same vessel.

14. The method of claim 12, wherein at least two of steps (a), (b), and (c) are conducted in the same vessel.

15. The method of claim 1, said method comprising a plurality of increasing temperatures between said first and second temperatures, and further comprising a plurality of increasing pressures between said first and second pressures.

16. The method of claim 1, wherein said first temperature and said second temperature are about the same.

17. The method of claim 1, wherein said first pressure and said second pressure are about the same.

18. The method of claim 12, wherein said converting is conducted at a temperature that is about the same as said first temperature, and is further conducted at a pressure that is about the same as said first pressure.

19. The method of claim 12, wherein said converting is conducted at a temperature that is about the same as said second temperature, and is further conducted at a pressure that is about the same as said second pressure.

20. The method of claim 12, wherein said at least one $C_1$-$C_4$ alcohol includes ethanol.

21. The method of claim 20, wherein the selectivity of ethanol produced by said activated catalyst is higher than the selectivity of ethanol that would have been produced in the absence of step (a).

22. The method of claim 20, wherein the yield of ethanol produced by said activated catalyst is higher than the yield of ethanol that would have been produced in the absence of step (a).

23. The method of claim 20, wherein the selectivity of $CO_2$ produced by said activated catalyst is lower than the selectivity of $CO_2$ that would have been produced in the absence of step (a).

24. A method of activating a catalyst, said method comprising:
   (a) contacting said catalyst with a first gas phase comprising syngas, under conditions comprising a first temperature of less than about 450° C. and a first pressure of less than about 200 atm, thereby producing a pre-activated catalyst; and
   (b) annealing said pre-activated catalyst with a second gas phase consisting essentially of an inert gas, under effective conditions comprising a second temperature of from about 150° C. to about 350° C. and a second pressure of from about 30 atm to about 200 atm, thereby producing an activated catalyst.

25. A method of activating a Co/Mo/S/K catalyst, said method comprising:
   (a) annealing said catalyst with helium at a temperature of about 310° C. and a pressure of about 1270 psi, thereby producing an annealed catalyst; and
   (b) contacting said annealed catalyst with syngas at a temperature of about 280° C. and a pressure of about 1270 psi, thereby producing an activated Co/Mo/S/K catalyst.

26. A method of producing an annealed catalyst intermediate, said method comprising:
   (a) providing an effective starting catalyst composition; and
   (b) annealing said starting catalyst composition with a first gas phase comprising an inert gas, under conditions including a temperature of less than about 450° C., thereby producing an annealed catalyst intermediate.

27. The method of claim 26 wherein said inert gas is selected from the group consisting of $N_2$, He, Ne, Ar, Kr, Xe, Rn, and combinations thereof.

28. The method of claim 27, wherein said inert gas is He.

29. The method of claim 26, wherein said annealing step comprises contacting said catalyst with $H_2$, CO, or a mixture of $H_2$ and CO.

30. The method of claim 29, wherein said annealing step further comprises contacting said catalyst with methane and/or carbon dioxide.

31. The method of claim 26, wherein said temperature is selected from about 280° C. to about 350° C.

32. The method of claim 26, wherein said effective conditions include a pressure of less than about 200 atm.

33. The method of claim 32, wherein said pressure is selected from about 80 atm to about 120 atm.

34. The method of claim 26, wherein said annealed catalyst intermediate comprises cobalt, molybdenum, sulfur, and potassium.

35. The method of claim 26, wherein step (b) is conducted for at least five hours.

36. The method of claim 26, further comprising converting syngas to at least one $C_1$-$C_4$ alcohol over a catalyst generated from said annealed catalyst intermediate.

37. The method of claim 36, wherein said at least one $C_1$-$C_4$ alcohol includes ethanol.

38. The method of claim 37, wherein the selectivity of ethanol produced by said catalyst is higher than the selectivity of ethanol that would have been produced in the absence of step (b).

39. The method of claim 37, wherein the yield of ethanol produced by said activated catalyst is higher than the yield of ethanol that would have been produced in the absence of step (b).

* * * * *